United States Patent
Inoue

(10) Patent No.: US 9,895,143 B2
(45) Date of Patent: Feb. 20, 2018

(54) MEDICAL SYSTEM AND METHOD OF CONTROLLING MEDICAL INSTRUMENTS

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 179 days.

(21) Appl. No.: 15/006,425

(22) Filed: Jan. 26, 2016

(65) Prior Publication Data

US 2016/0213364 A1 Jul. 28, 2016

Related U.S. Application Data

(63) Continuation of application No. PCT/JP2014/067795, filed on Jul. 3, 2014.

(30) Foreign Application Priority Data

Jul. 26, 2013 (JP) .................................. 2013-155772

(51) Int. Cl.
*G06F 19/00* (2011.01)
*A61B 17/00* (2006.01)
(Continued)

(52) U.S. Cl.
CPC ........ *A61B 17/00234* (2013.01); *A61B 1/008* (2013.01); *A61B 1/0052* (2013.01);
(Continued)

(58) Field of Classification Search
CPC . A61B 17/00234; A61B 34/70; A61B 1/0052; A61B 1/008; A61B 17/29;
(Continued)

(56) References Cited

U.S. PATENT DOCUMENTS

2007/0265502 A1 11/2007 Minosawa et al.
2010/0016666 A1 1/2010 Hasegawa
(Continued)

FOREIGN PATENT DOCUMENTS

CN 101340850 A 1/2009
CN 101444415 A 6/2009
(Continued)

OTHER PUBLICATIONS

International Search Report dated Sep. 16, 2014 issued in PCT/JP014/067795.

*Primary Examiner* — Ronnie Mancho
(74) *Attorney, Agent, or Firm* — Scully, Scott, Murphy & Presser, P.C.

(57) ABSTRACT

An object of the invention is to provide for automatic angular adjustment of an end effector thereby improving on the operability of a medical instrument. The medical system of the invention comprises a medical instrument including a driver for driving adjustment of the angle of the end effector relative to a shaft, a trocar having an insertion opening through which the medical instrument is inserted, a sensor that produces a sensor signal including at least an angle of a shaft in a reference coordinate system, and a driver for enabling follow-up control processing for driving the driver based on a sensor signal produced out of the sensor such that the angle of the end effector follows a follow-up criterion in a reference coordinate system.

12 Claims, 10 Drawing Sheets

(51) Int. Cl.
*A61B 1/005* (2006.01)
*A61B 1/008* (2006.01)
*A61B 17/29* (2006.01)
*A61B 17/34* (2006.01)
*A61B 34/00* (2016.01)
*A61B 90/00* (2016.01)
*A61B 34/30* (2016.01)

(52) U.S. Cl.
CPC .......... *A61B 17/29* (2013.01); *A61B 17/3421* (2013.01); *A61B 34/70* (2016.02); *A61B 2017/2927* (2013.01); *A61B 2017/2947* (2013.01); *A61B 2034/305* (2016.02); *A61B 2090/062* (2016.02); *A61B 2090/067* (2016.02); *A61B 2090/0811* (2016.02)

(58) Field of Classification Search
CPC .......... A61B 17/3421; A61B 2034/305; A61B 2090/062; A61B 2090/067; A61B 2090/0811; A61B 2017/2927; A61B 2017/2947
USPC ........................................................ 700/258
See application file for complete search history.

(56) References Cited

U.S. PATENT DOCUMENTS

| | | | | |
|---|---|---|---|---|
| 2012/0010615 A1* | 1/2012 | Cummings | ........ | A61B 18/1445 606/51 |
| 2012/0010616 A1* | 1/2012 | Huang | ............... | A61B 18/1445 606/52 |
| 2012/0078248 A1* | 3/2012 | Worrell | .............. | A61B 18/1445 606/45 |
| 2013/0131651 A1* | 5/2013 | Strobl | .................... | A61B 17/00 606/1 |
| 2014/0239038 A1* | 8/2014 | Leimbach | ........ | A61B 17/07207 227/175.1 |
| 2014/0246471 A1* | 9/2014 | Jaworek | ........... | A61B 17/07207 227/175.1 |
| 2014/0246473 A1* | 9/2014 | Auld | .................... | A61B 17/068 227/175.1 |
| 2014/0246474 A1* | 9/2014 | Hall | ................. | A61B 17/07207 227/175.1 |
| 2014/0246475 A1* | 9/2014 | Hall | ..................... | A61B 17/068 227/175.1 |
| 2014/0246476 A1* | 9/2014 | Hall | ..................... | A61B 17/068 227/175.1 |
| 2014/0246477 A1* | 9/2014 | Koch, Jr. | ............. | A61B 17/068 227/180.1 |
| 2014/0246478 A1* | 9/2014 | Baber | .................. | A61B 17/068 227/180.1 |
| 2014/0246479 A1* | 9/2014 | Baber | .................. | A61B 17/068 227/180.1 |
| 2014/0249557 A1* | 9/2014 | Koch, Jr. | ............. | A61B 17/072 606/170 |
| 2014/0263537 A1* | 9/2014 | Leimbach | ........ | A61B 17/07207 227/175.1 |
| 2014/0263538 A1* | 9/2014 | Leimbach | ........ | A61B 17/07207 227/175.1 |
| 2014/0263542 A1* | 9/2014 | Leimbach | ............ | A61B 17/064 227/175.2 |
| 2014/0263543 A1* | 9/2014 | Leimbach | ............ | A61B 17/068 227/175.2 |
| 2014/0263553 A1* | 9/2014 | Leimbach | ............ | A61B 17/068 227/176.1 |
| 2014/0263554 A1* | 9/2014 | Leimbach | ............ | A61B 17/068 227/176.1 |
| 2014/0263564 A1* | 9/2014 | Leimbach | .............. | A61B 34/30 227/180.1 |
| 2014/0263565 A1* | 9/2014 | Lytle, IV | ............. | A61B 17/068 227/180.1 |
| 2014/0277017 A1* | 9/2014 | Leimbach | ........ | A61B 17/07207 606/167 |
| 2016/0213436 A1* | 7/2016 | Inoue | ................. | A61B 17/3421 |
| 2016/0270780 A1* | 9/2016 | Hall | ..................... | A61B 17/072 |
| 2017/0007255 A1* | 1/2017 | Jaworek | ........... | A61B 17/07207 |

FOREIGN PATENT DOCUMENTS

| | | |
|---|---|---|
| JP | 2002-360594 | 12/2002 |
| JP | 2004-135781 A | 5/2004 |
| JP | 3683554 B2 | 8/2005 |
| JP | 2007-301378 | 11/2007 |
| JP | 4014792 B2 | 11/2007 |
| WO | WO 2008/120508 A1 | 10/2008 |

* cited by examiner

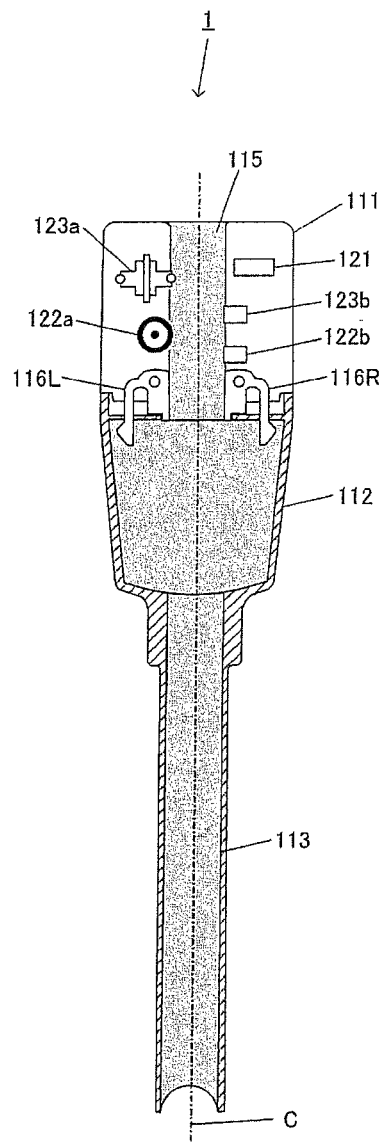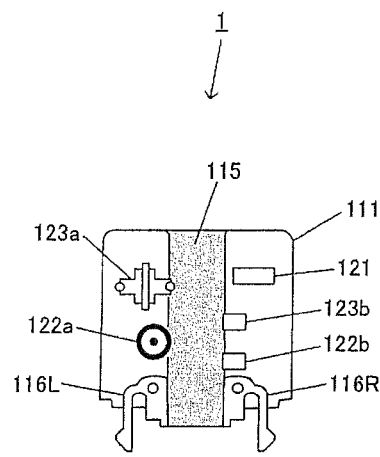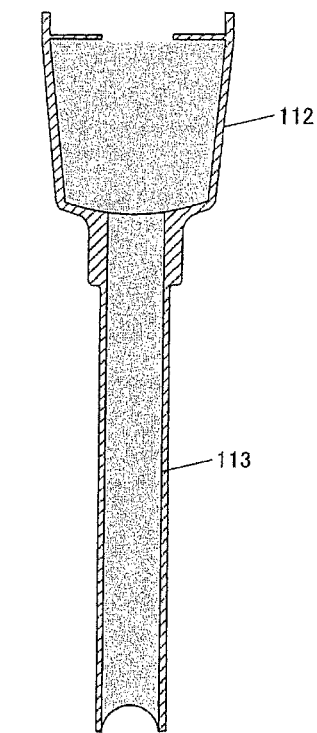
FIG.3A  FIG.3B

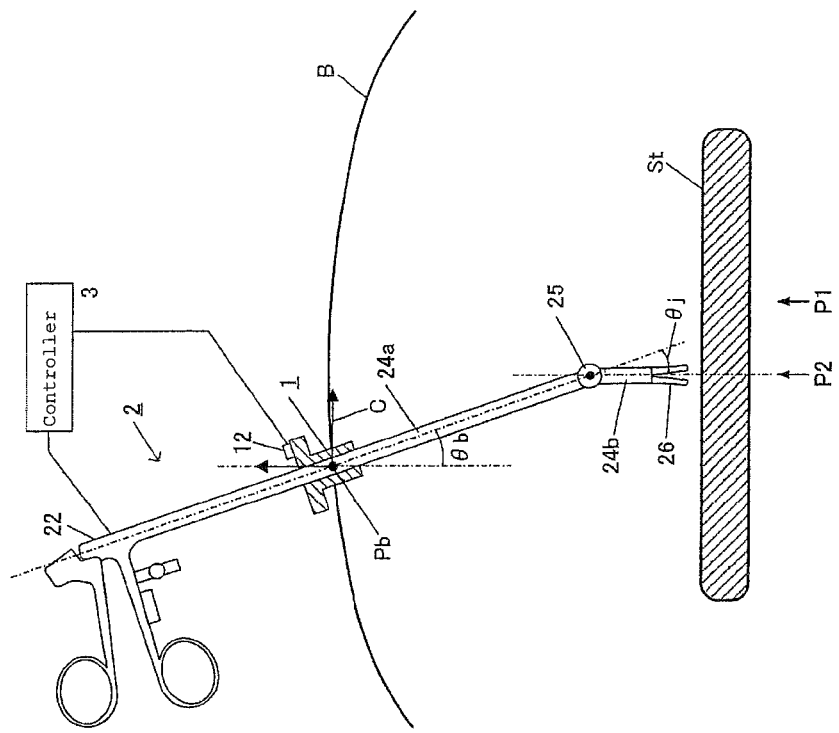
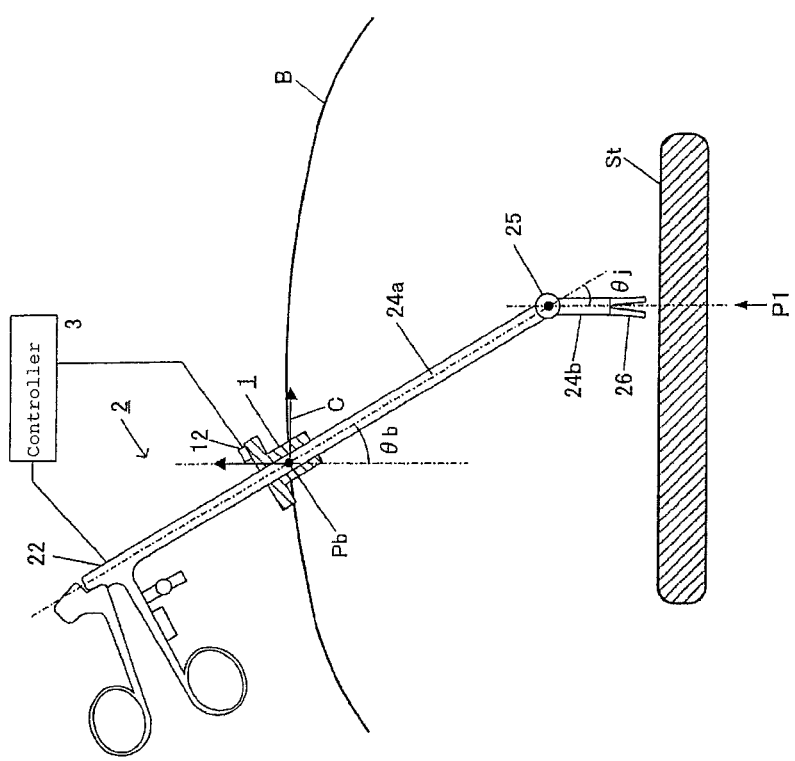
FIG.7A
FIG.7B

MEDICAL SYSTEM AND METHOD OF CONTROLLING MEDICAL INSTRUMENTS

CROSS-REFERENCE TO RELATED APPLICATIONS

This application is a continuation claiming priority on the basis of Japan Patent Application No. 2013-155772 applied in Japan on Jul. 26, 2013 and based on PCT/JP2014/067795 filed on Jul. 3, 2014. The contents of both the PCT application and the Japan Application are incorporated herein by reference.

BACKGROUND OF THE INVENTION AND RELATED ART STATEMENT

The present invention relates to a medical system making use of a medical instrument that is inserted through the body of a patient during surgical operation for in vivo treatments, in vivo viewing, etc., and a method of controlling a medical instrument.

There is laparoscopic surgery now available wherein various medical instruments inserted through a trocar passed from the body surface of a patient through the body cavity apply various surgical treatments and medical examinations in the body of the patient. Although this laparoscopic surgery is less invasive of patients due to the fact that the size of the body surface site to be cut open may be small, much is left to be desired in the visibility of an endoscope and the operability of medical instruments because there is the need of applying treatments while performing in vivo viewing using the endoscope.

Japanese Patent No. 4014792 discloses that the driver of a treatment portion is driven such that the degree-of-freedom configurations of the treatment portion and an operating portion are aligned in such a way as to make a posture of a medical instrument in the treatment portion identical with a posture of the medical instrument in the operating portion, thereby improving on the operability of the medical instrument.

Japanese Patent No. 3683554 discloses a surgical robot comprising a mode changeover means for changing a joint assembly of a medical instrument from a free state where the joint assembly is capable of free movement to a fixedly locked state where the joint assembly is fixed in place, and a pressure detector means provided on an outer wall surface of a trocar for controlling the motion changeover means based on the result of detection.

SUMMARY OF THE INVENTION

A medical system according to one aspect of the invention comprises:

a medical instrument including a shaft coupled to a grip grasped by a practitioner, an end effector located at a distal end of the shaft, a moving joint assembly for adjusting an angle of the end effector relative to the shaft, and a driver for driving the moving joint assembly, a trocar having an insertion opening through which the medical instrument is inserted, a sensor assembly for producing a sensor signal including at least an angle of the shaft in a reference coordinate system, and a controller that enables follow-up processing for driving the driver such that based on a sensor signal produced out of the sensor assembly, the angle of the end effector follows a follow-up criterion in the reference coordinate system.

The invention also provides a method of controlling a medical instrument which includes a shaft coupled to a grip grasped by a user, an end effector located at a distal end of the shaft, a moving joint for adjusting an angle of the end effector relative to the shaft, and a driver for driving the moving joint, includes driving the driver such that an angle of the end effector follows a follow-up criterion in a reference coordinate system based on a sensor signal including at least an angle of the shaft in the reference coordinate system, when the shaft inserted through an insertion opening in a trocar.

BRIEF EXPLANATION OF THE DRAWINGS

FIGS. 3A and 3B are illustrative of the internal construction of the trocar according to one embodiment of the invention.

FIGS. 7A and 7B are illustrative of the control mode (Example 1) of the medical instrument according to one embodiment of the invention.

DETAILED DESCRIPTION OF EMBODIMENTS

Figure 1:
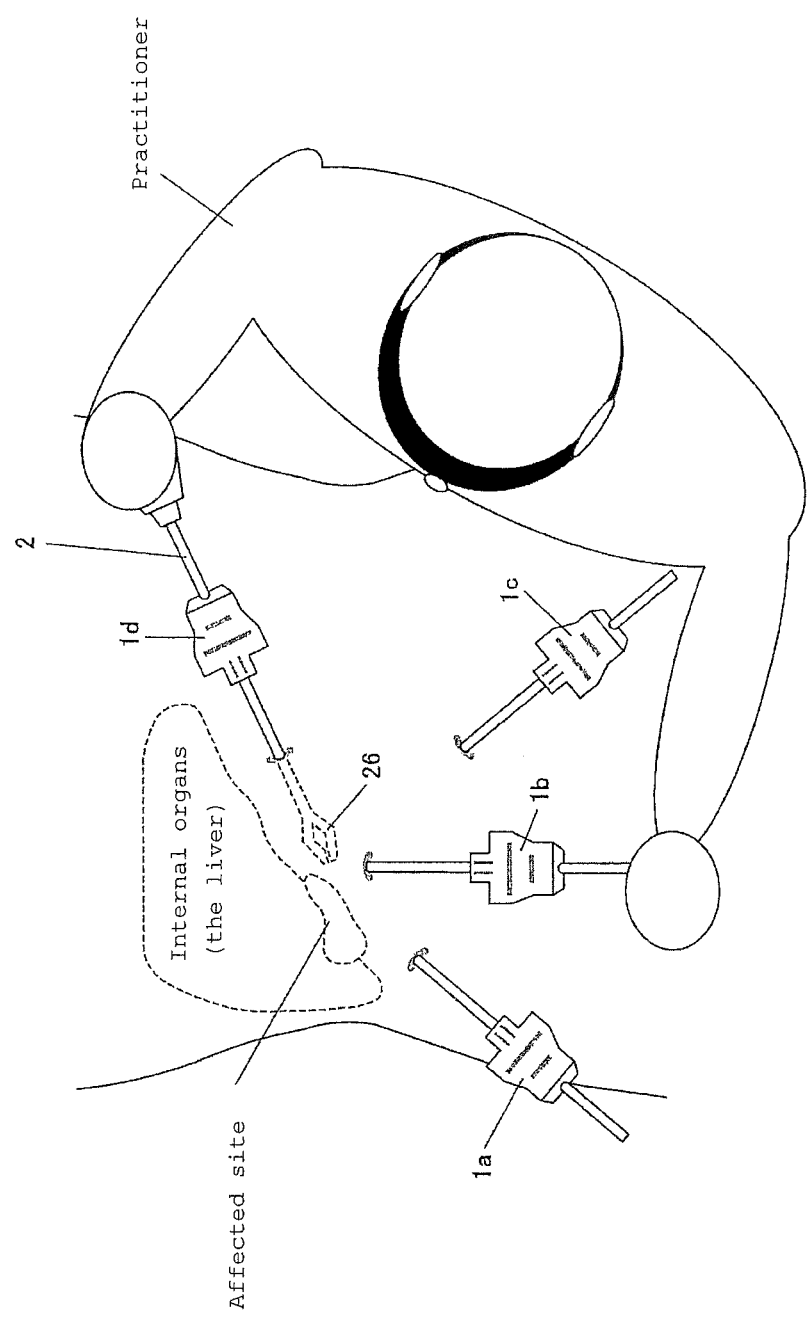
FIG. 1 is illustrative of how laparoscopic surgery is performed using a medical instrument (a pair of forceps).

FIG. 1 is illustrative of how laparoscopic surgery is performed using the forceps 2. In typical laparoscopic surgery, there are multiple openings cut open in the abdomen, etc. of a patient, through which various medical instruments such as an imager (imaging device), forceps and a (electric) knife are inserted to check on images taken by the imager for viewing and surgically treating an affected site or lesion. This laparoscopic surgery can be less invasive of patients because the area to be cut open is small.

In laparoscopic surgery, tubes called the trocars (channels) 1a to 1d are put in openings provided in the body wall of a patient, and various medical instruments are inserted through the patient's body via the trocars 1a to 1d. Forceps 2 (medical instrument) are shown to be put in the trocar 1d. The forceps 2 placed in the patient's body via the trocar 1d is provided at a distal end with a distal-end grip 26 acting as an end effector so that a practitioner (user) can operate the forceps 2 to open or close the distal-end grip 26 for applying surgical treatments to the affected site.

In conventional medical instruments, the end effector such as the distal-end grip 26 is capable of angular adjustment in the patient's body so as to improve the operability of the practitioner. The practitioner may operate the end effector to adjust its angle. For laparoscopic surgery performed in the patient's body, it is required for the practitioner to operate the medical instrument while checking on the in vivo states of the patient through an endoscope or the like. The angular adjustment of the end effector in the medical instrument including an endoscope is difficult and requires some considerable skill. An object of the invention is to make improvements in angular adjustment of medical instruments. The medical instrument may have various forms of not only a pair of forceps 2 (with a distal-end grip 26 as an end effector) shown in FIG. 1 but also an endoscope (with an imager as an end effector) and an electric knife (with a laser head as an end effector).

Figure 2:
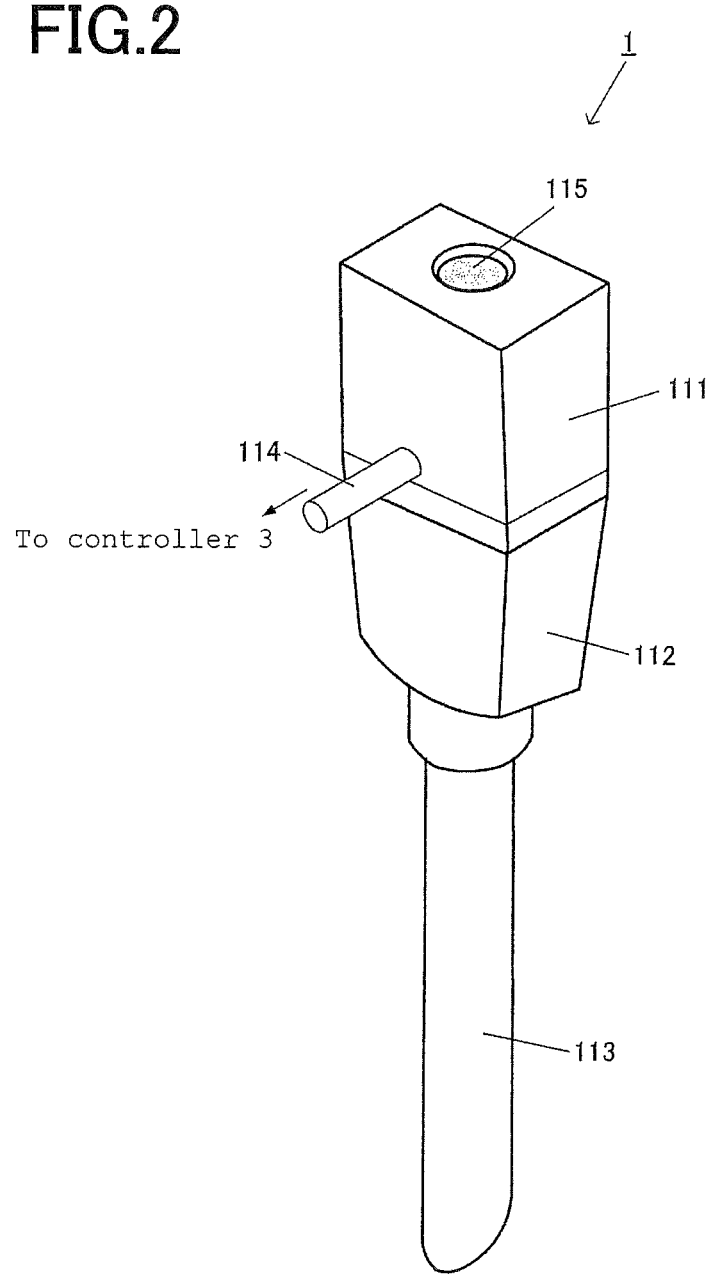
FIG. 2 is illustrative of the outside appearance of the trocar according to one embodiment of the invention.

FIG. 2 is illustrative of the outside appearance of the trocar 1 used with the medical system according to the embodiment described here. This trocar 1 includes an upper housing 111, a lower housing 112 and a tubular member 113. The upper housing 111 is provided with an opening 115 for insertion of various medical instruments. The tubular member 113 will be inserted in the patient's body. A medical instrument inserted from the opening 115 (hereinafter called the insertion opening 115) passes through the lower housing 112 and tubular member 113, and is inserted from the lower end of the tubular member 113 into the patient's body for in vivo viewing and in vivo treatments.

Within the upper housing 111 there are various sensors disposed for detection of a state of the trocar 1 and a state of a medical instrument inserted from the insertion opening 115. Output signals from various sensors are sent out to a controller 3 by way of a cable 114. Note here that the cable 114 also serves as a power supply to various sensors. Communications between various sensors and the controller 3 may be made by way of such a wire; however, they may be wireless or, alternatively, they may be driven by a battery for removal of the cable 114 from the trocar 1.

FIGS. 3A-3B are sectional views of the internal construction of the trocar 1 according to the embodiment described here. Referring to FIG. 2, the upper housing 111 is described as being provided with the insertion opening 115. A portion colored in gray in FIG. 2, i.e., a portion from the insertion opening 115 to the lower end of the tubular member 113 is a hollow portion to receive various medical instruments. The upper housing 111 may be coupled to or decoupled from the lower housing 112 by means of couplers 116R and 116L each in a clip form. During use of the trocar 1, the upper housing 111 remains coupled to the lower housing 112 by means of the couplers 116R and 116L as shown in FIG. 3A, and for cleaning or other purposes, the upper housing 111 may be decoupled from the lower housing 112, as shown in FIG. 3B. Such coupling/decoupling makes sure easy cleaning, disinfection and replacement of the tubular member 113, and easy maintenance of the upper housing 111 containing various sensors as well. Note here that the trocar 1 may be made up of a single unit where the upper housing 111 is integral with the lower housing 112.

Referring to the trocar 1 according to the embodiment described here, there are various sensors (a trocar sensor assembly 12) housed within the upper housing 111. The trocar sensor assembly 12 includes a tilt angle detection sensor 121, an amount-of-movement detection sensor 122 for detection of the amount of movement, and an amount-of-rotation detection sensor 123. The tilt angle detection sensor 121 is provided for detection of a tilt angle indicative of which direction the trocar 1 points in relative to a reference coordinate system. Note here that the reference coordinate system refers to a coordinate system defined for a fixed object such as a patient or a ground plane (see a symbol C in FIGS. 7A-7B), and various sensors such as an acceleration sensor may be used as the tilt angle detection sensor 121. The acceleration sensor may detect an acceleration applied on it to sense which direction the trocar 1 points in, viz., the angle of tilt relative to the reference coordinate system.

The amount-of-movement detection sensor 122 for detection of the amount of movement is provided to detect the amount of advancement or retraction of the medical instrument through the trocar 1 in the direction of insertion (vertical direction in FIGS. 3A and 3B). As described with reference to FIG. 1, a practitioner like a surgeon inserts or extracts the medical instrument through the trocar 1 for movement to a proper site in the patient's body. The amount-of-movement detection sensor 122 may detect the position of the medical instrument inserted through the trocar 1 as an amount of movement. In FIG. 3A, the center axis C of the trocar 1 in the direction of insertion is indicated by an alternate long and short dash line. The amount-of-movement detection sensor 122 detects the amount of movement of the medical instrument in parallel with the center axis C as the amount of movement. In the embodiment described here, the amount-of-movement detection sensor 122 is made up of an amount-of-movement detection roller 122a combined with a photosensor 122b.

The amount-of-rotation detection sensor 123 is provided to detect the amount of rotation of the medical instrument rotating in association with operation by a practitioner or the like. By rotating the medical instrument inserted through the insertion opening 115 about the center axis C, it is possible to change the orientation of the end effector attached to the distal end of the medical instrument in the patient's body. The amount-of-rotation detection sensor 123 may detect this amount of rotation thereby detecting which orientation the end effector of the medical instrument points in. The amount-of-rotation detection sensor 123 here may be made up of an amount-of-rotation detection roller 123a combined with a photosensor 123b.

Figure 4:
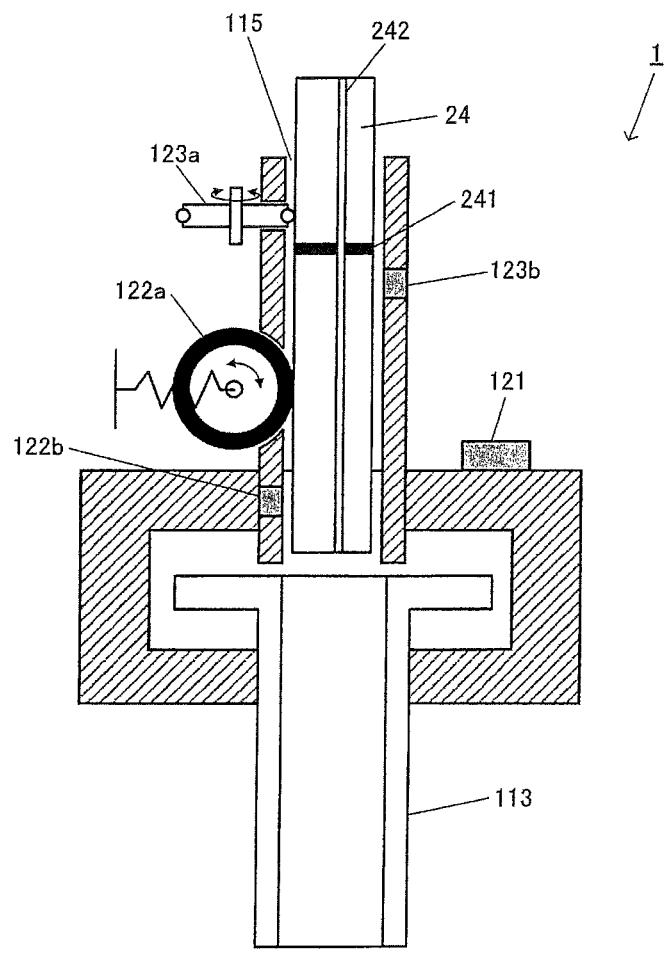
FIG. 4 is illustrative of the construction of the trocar sensor assembly according to one embodiment of the invention.

Referring to the trocar 1 having the internal construction as described above, the trocar sensor assembly 12 located within the trocar 1 sends a detection signal out to the controller 3 by way of a communication unit 13 not shown in FIGS. 3A-3B. The actuation of the trocar sensor assembly 12 in the embodiment described here is explained with reference to FIG. 4 that is illustrative in schematic of the construction of the trocar sensor assembly 12. FIG. 4 is illustrative in schematic of the construction of the trocar sensor assembly 12 disposed within the trocar 1 shown in FIGS. 3A and 3B, and shows that the first shaft 24 of the medical instrument is inserted through the trocar 1. Note here that the end effector attached to the distal end of the medical instrument or the like is not shown in FIG. 4.

The diameter of the insertion opening 115 in the trocar 1 is somewhat larger than the portion, such as the first shaft 24, of the medical instrument to be inserted in place so that the medical instrument can be inserted through it. Although the trocar 1 will be fixed in the vicinity of the patient's body surface, it is pivotally rotated in operable association with the operation of the medical instrument with a certain point as a reference. The tilt angle detection sensor 121 fixed on the housing of the trocar 1 may detect pivotal rotation of the trocar 1 thereby detecting the direction of the trocar 1 in the reference coordinate system, viz., the direction of the medical instrument.

As already explained with reference to FIGS. 3A-3B, the amount-of-movement detection sensor 122 is made up of the amount-of-movement detection roller 122a combined with the photosensor 122*b*. The amount-of-movement detection roller 122*a* is a roller that has an axis of rotation in a plane vertical to the sheet plane of FIG. 4. This amount-of-movement detection roller 122*a* is biased by a resilient member such as a spring toward the insertion opening 115 side so that it comes in contact with the surface of the medical instrument (first shaft 24) inserted through the insertion opening 115 to convert the amount of movement of the medical instrument into the amount of its rotation. The rotating shaft of the amount-of-movement detection roller 122*a* is provided with an encoder that produces the amount of rotation of the amount-of-movement detection roller 122*a* as the amount of movement. In the embodiment described here, the photosensor 122*b* is positioned facing the inside of the insertion opening 115 to calibrate the amount of movement (or set it to the initial value). This photosensor 122*b* detects a position-of-movement detecting mark 241 provided on the medical instrument side (or the first shaft 24 side or the like) so that the amount of movement detected by the amount-of-movement detection roller 122*a* is calibrated. Accordingly, when the medical instrument advances or retracts through the insertion opening 115, the amount of movement is calibrated (or set to its initial value) each time the position detection mark 241 passes through the photosensor 122*b* so that the precise amount of movement of the medical instrument relative to the trocar 1 can be detected.

The amount-of-rotation detection sensor 123 in the embodiment described here is made up of the amount-of-rotation detection roller 123*a* with the photosensor 123*b* as explained with reference to FIGS. 3A-3B. The amount-of-rotation detection roller 123*a* has a rotating shaft pointing in the vertical direction of FIG. 4. The amount-of-rotation detection roller 123*a* is biased by a resilient member such as a spring toward the insertion opening 115 so that it comes into contact with the surface of the medical instrument (first shaft 24) inserted through the insertion opening 115 to convert the amount of rotation of the medical instrument into the amount of rotation of the amount-of-rotation detection roller 123*a*. Note here that the contact surface of the amount-of-rotation detection roller 123*a* is preferably provided with a member (such as a bearing) that does not disturb the movement of the medical instrument in the insertion direction. The amount-of-rotation detection roller 123*a* is provided at the rotating shaft with an encoder that produces the amount of rotation of the amount-of-rotation detection roller 123*a* in the form of the amount of rotation of the medical instrument. In the embodiment described here, the photosensor 123*b* facing the inside of the insertion opening 115 is provided to calibrate the amount of rotation (or set it to the initial value). This photosensor 123*b* detects a position-of-rotation detecting mark 242 provided on the medical instrument side (the first shaft 24 or the like) so that the amount of rotation detected by the amount-of-rotation detection roller 123*a* can be calibrated as is the case with the amount-of-movement detection sensor 122.

While the trocar sensor assembly disposed within the trocar 1 is explained, it is to be understood that the sensor may be configured in various forms. In the embodiment described here, for instance, a mechanical sensor configuration using a roller is adopted to detect the amount of movement and the amount of rotation. It is to be understood, however, that an optical sensor capable of detecting the amount and direction of movement of a surface, for instance, an optical sensor used with a laser mouth may also be used for detection of the amounts of movement and rotation. In that case, just one optical sensor may be used to detect the amount of movement and the amount of rotation. For the medical system according to the embodiment described here, it is necessary to determine the direction or the direction and position of the medical instrument inserted through the patient's body. In the embodiment described here, these are detected by various sensors housed within the trocar 1 in view of ease of handling; however, the direction or the direction and position of the medical instrument may be detected by sensors located outside of the trocar 1. For instance, the tilt angle detection sensor 121 located within the trocar 1 may be located directly on the medical instrument side.

Figure 5A:
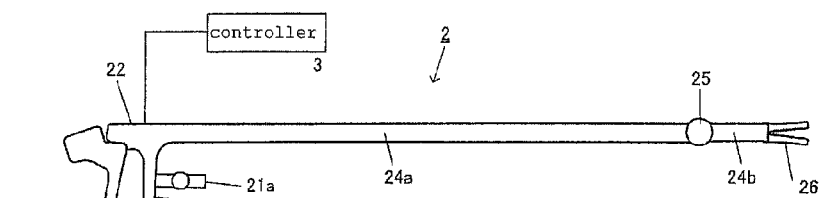
FIGS. 5A, 5B and 5C are illustrative of the construction and control mode of the medical instrument (forceps) according to one embodiment of the invention.
Figure 5B:
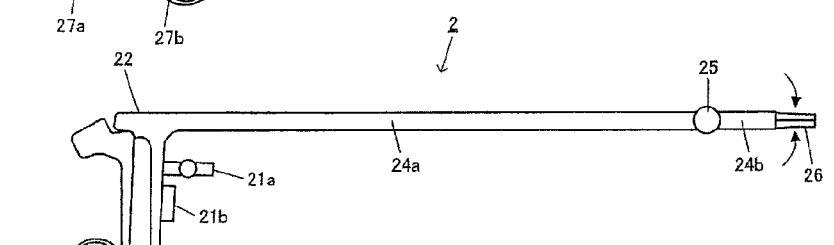
Figure 5C:
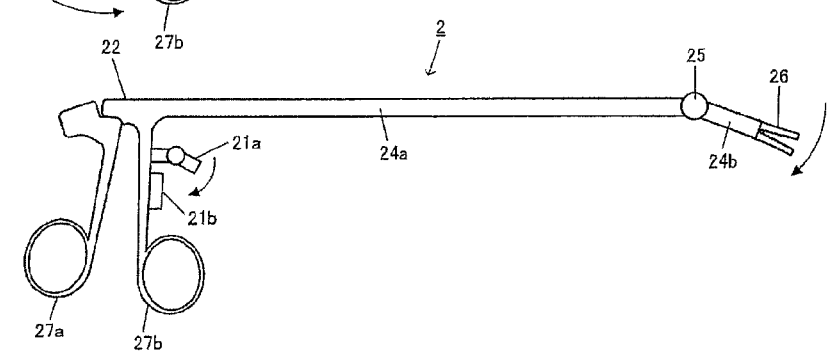

The medical instrument(s) used in the medical system according to one embodiment of the invention is now explained. FIGS. 5A-5C are illustrative of the construction and control mode of the medical instrument 2 (forceps) according to one embodiment of the invention. In the embodiment described here, the medical instrument 2 performs various treatments in the patient's body, and comprises a distal-end grip 26 as an end effector. This distal-end grip 26 comprises a pair of grip members 27*a* and 27*b* put by a string (such as a wire or thread) in coordinated operation. As depicted in FIG. 5A, the distal-end grip 26 remains open while the grip members 27*a* and 27*b* are spaced away from each other, and as depicted in FIG. 5B, the distal-end grip 26 remains closed while the grip members 27*a* and 27*b* get proximate to each other. The practitioner may open or close the grip members 27*a* and 27*b* while gripping them to operate the opening and closing of the distal-end grip 26.

In the embodiment described here, the forceps 2 include a first shaft 24*a* and a second shaft 24*b* capable of rotation by way of a moving joint 25. As the moving joint 25 is rotated using the driver 22 built in the main body of the medical instrument 2, it may cause the second shaft 24*b* to which the distal-end grip 26 (end effector) is attached to rotate relative to the first shaft 24*a*. The driver 22 may be a motor or otherwise constructed in various configurations capable of generating driving force in response to a control signal from the controller 3. The driving force generated in the driver 22 is transmitted to the moving joint 25 via a driving force transmission means such as a gear, a wire or a thread to rotate the second shaft 24*b* to which the distal-end grip 26 is attached. In the embodiment described here, the driver 22 is shown to be built in the main body of the medical instrument 2; however, it may be located outside of the main body of the medical instrument 2. FIG. 5A shows one exemplary mode of connecting the medical instrument 2 to the controller 3. The connection mode to the controller 3 is the same as in FIGS. 5B and 5C although not shown. In the embodiment described here, a direction input 21*a* is provided on the grip member 27*b*. As the direction input portion 21*a* is operated, it causes an operational signal to be sent to the controller 3 that in turn drives the driver 22 for control of rotation of the moving joint 25. In the embodiment described here, the driver 22 may be controlled in a spontaneous way, viz., without recourse to the operation of the direction input portion 21*a*. As the direction input portion 21*a* in a stick form is operated as shown in FIG. 5C, it causes the driver to rotate the moving joint 25 in association with its operating direction, resulting in a change in the orientation of the distal-end grip 26. While the moving joint 25 is shown to be capable of two-dimensional motion on the sheet plane, it is to be noted that it is also capable of three-dimensional motion including a direction diagonal to the sheet plane.

While the medical instrument 2 (forceps) according to the embodiment described here is shown to use just one moving joint 25 for control of the orientation of the distal-end grip 26 (end effector), it is to be understood that the direction or orientation control of the distal-end grip 26 may be carried out by multiple moving joints.

Figure 6:
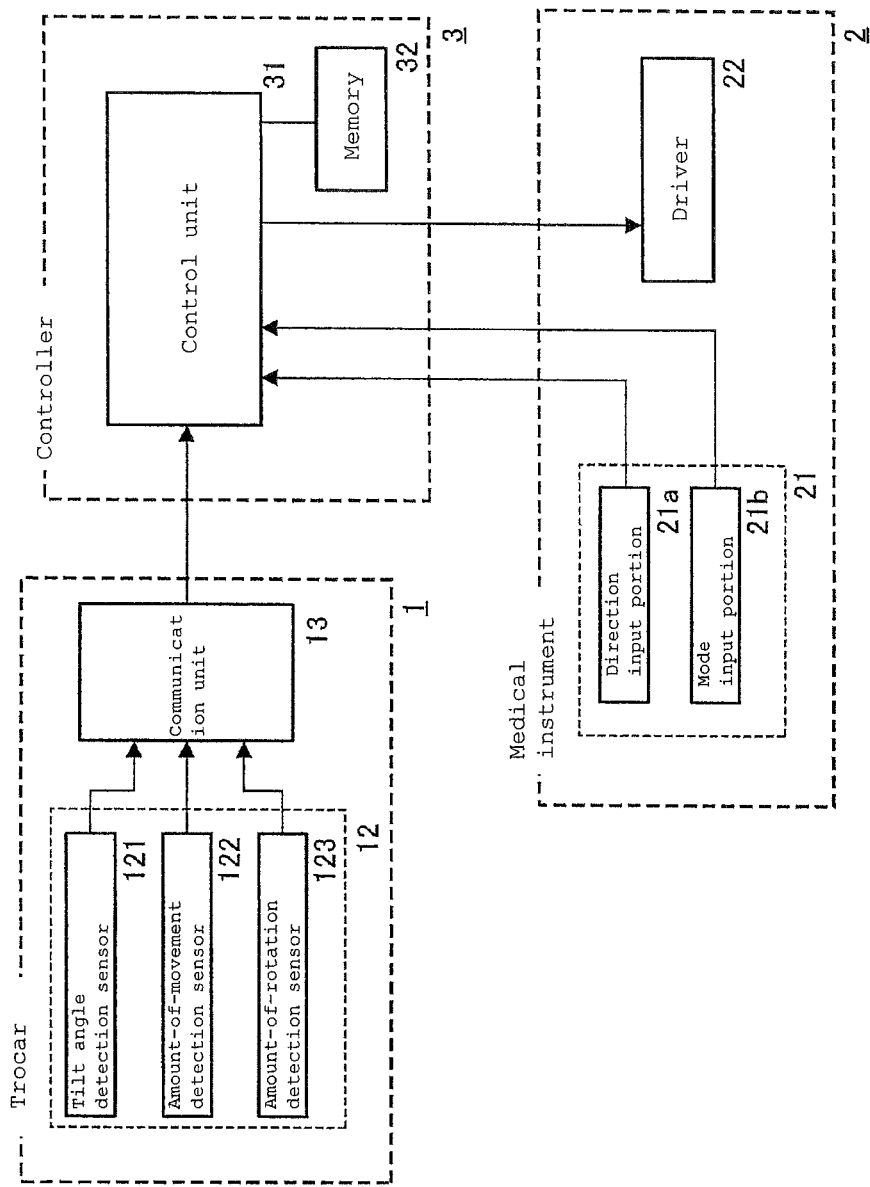
FIG. 6 is a block diagram for the control configuration of the medical system according to one embodiment of the invention.

FIG. 6 is a block diagram for the control configuration of the medical system according to one embodiment of the invention. This medical system includes the trocar 1 explained with reference to FIGS. 2, 3A, 3B and 4, the medical instrument 2 explained with reference to FIGS. 5A-5C, and the controller 3. The trocar 1 includes the trocar sensor assembly 12 including the tilt angle detection sensor 121, the amount-of-movement detection sensor 122, the amount-of-rotation detection sensor 123, and the communication unit. Note here that although depending on the control mode, all of the (three) sensors are not necessarily used for the trocar sensor assembly 12. The control mode will be described later. On the other hand, the medical instrument 2 includes the operation input portion 21 and the driver 22, wherein the operation input portion 21 includes the direction input portion 21a explained with reference to FIGS. 5A-5C and a mode input portion 21b. The mode input portion 21 is the operating portion located on the grip member 27b, as shown in FIGS. 5A-5C. In the embodiment described here, this operating portion is used for a changeover between various modes implemented in the medical system. The driver 22 may be made up of a motor or other member capable of generating driving force to the moving joint 25 of the medical instrument.

The trocar 1 and medical instrument 2 are connected to the controller 3. The controller 3 includes a control unit 31 constructed of a CPU or the like, and a memory 32 serving as a storage. Various programs running on the medical system may be stored in the memory 32 in which various signals and data necessary for running programs may also be stored.

The controller 3 according to the embodiment described here may be implemented in two modes. In one (operating) mode, the direction input portion 21a of the medical instrument is operated such that the moving joint 25 is rotated to adjust the angle of the end effector. In this operating mode, the practitioner may operate the direction input portion 21a such that the moving joint 25 is rotated to adjust the angle of the distal-end grip 26 (end effector) as explained with reference to FIG. 5C. While viewing affected sites or lesions in the body through the endoscope or the like, the practitioner may operate the direction input portion 21a to turn the distal-end grip 26 in a proper direction.

In another (follow-up) mode, follow-up processing is implemented such that the angle of the distal-end grip 26 (end effector) is adjusted in a proper direction without recourse to operating the direction input portion 21a. In this follow-up mode, the driver 22 is driven such that the angle of the end effector of the medical instrument (here the distal-end grip 26) traces up the follow-up criterion set relative to the reference coordinate system (reference surface or reference point). Note here that the reference coordinate system is defined for a fixed object such as a patient or a ground plane, as explained with reference to the sensor assembly of the trocar 1.

FIGS. 7A-7B show a follow-up control mode (Example 1) for the medical instrument 2 (forceps) explained with reference to FIGS. 5A-5C. Being put into the patient's body surface B, the trocar 1 communicates the patient's body surface B with the interior of the body through the insertion opening 115. The medical instrument 2 (forceps) is inserted through the insertion opening 115 in the trocar 1, allowing the distal-end grip 26 to apply medical treatments to an affected site. The medical instrument 2 and trocar sensor assembly 12 are connected to the controller 3 that may detect various states of the trocar 1 and medical instrument 2, and may drive and control the driver 22 of the medical instrument 2 as well. In this follow-up mode, a reference surface St that is the surface of the affected site is set as the follow-up criterion. The moving joint 25 is driven and controlled such that the distal-end grip 26 points in a direction orthogonal to the reference surface St. The direction in which the distal-end grip 26 as the end effector points is judged on the basis of a sensor signal produced out of the trocar sensor assembly 12. Note here that a symbol θb in FIGS. 7A-7B stands for the angle of the first shaft 24a with respect to the reference coordinate system C, a symbol θj stands for the control angle of the moving joint 25 in the follow-up processing, and symbols P1 and P2 are indicative of the point of intersection of the direction in which the distal-end grip 26 points with the reference surface St.

When the medical instrument 2 is moved from the state of FIG. 7A to the state of FIG. 7B, the distal-end grip 26 is held in a direction orthogonal to the reference surface St in either case. On the basis of the sensor signal detected by the trocar sensor assembly 12, the controller 3 determines the direction in which the first shaft 24a points to control the driver 22 for rotation of the moving joint 25. Thus, the controller 3 adjusts and controls the driver 22 such that the distal-end grip 26 forms a given angle (here orthogonal to the reference surface St) with the reference surface St. While the motion of the moving joint 25 is explained in FIGS. 7A-7B as two-dimensional motion on the sheet plane, it is to be understood that the follow-up processing may also keep up with three-dimensional motion including a direction orthogonal to the sheet surface, too.

Referring to the control configuration of FIG. 6, as the follow-up mode is designated at the mode input portion 21b, it permits the controller 3 to execute follow-up control of the driver 22 on the basis of a sensor signal produced out of the trocar sensor assembly 12, instead of control of the driver 22 on the basis of an operational signal from the direction input portion 21a (angular adjustment of the moving joint 25). Stored in the memory 32 of the controller 3 is the follow-up criterion set on the reference coordinate system. In the follow-up mode, the driver 22 is controlled on the basis of the sensor signal and the follow-up criterion such that the end effector of the medical instrument 2 has a given position relation to that follow-up criterion.

Possible follow-up criteria used in the follow-up mode may include a criterion set by detection of states of the medical instrument 2, a criterion set by permitting the practitioner to operate a setting input portion provided for setting the criterion in the operation input portion 21, or a criterion set on the basis of results detected by various sensors such as the endoscope. In the control flow explained with reference to FIG. 8, a state of the medical instrument 2 is acquired upon a changeover from the operating mode to the follow-up mode, and a follow-up criterion is set on the basis of that state.

While the surface of the affected site is here set as the reference surface St, it is to be understood that the reference surface may be a virtual surface rather than a real surface such as the surface of the affected site. It is also to be noted that the angle of the end effector is not always orthogonal to the reference surface St; it may tilt by a given angle with respect to the reference surface St. The reference surface St may also be defined as a curved surface rather than a plane. For instance, a curved surface of the affected site taken by an endoscope inserted through the patient's body apart from the medical instrument 2 may be set as the reference surface St.

The trocar 1 is capable of pivotal rotation about a pivotal point Pb. On the basis of the sensor signal from the trocar sensor assembly 12 and the amount-of-rotation information from the moving joint 25, the direction in which the distal-end grip 26 points may be detected. While three different sensors are explained for the trocar sensor assembly 12 with reference to FIG. 6 and so on, it is noted that at least a tilt angle detection sensor 121 is required so as to detect the direction in which the distal-end grip 26 points. In the control mode described here, the tilt angle detection sensor 121 may be located on the medical instrument 2 to detect the direction in which the distal-end grip 26 points. With the tilt angle detection sensor 121 mounted on the first shaft 24*a*, it is possible to detect the direction in which the distal-end grip 26 points on the basis of that tilt angle detection sensor 121 and the amount of rotation of the moving joint 25.

With the medical system according to the embodiment described here, it is thus possible to permit the direction in which the end effector points to follow the follow-up criterion (here the reference surface St) set on the reference coordinate system thereby improving on practitioner's operability. The mode of permitting the angle of the end effector to follow the reference surface St is best suited for peeling of the skin of an internal organ by the distal-end grip 26 or incising of the skin by means of a medical knife or the like. With the medical instrument 2 (the endoscope) whose end effector includes an imager, it is possible to improve on visibility because the imager and the surface to be viewed are held at a constant angle over a wide viewing range for an internal organ.

Figure 8:
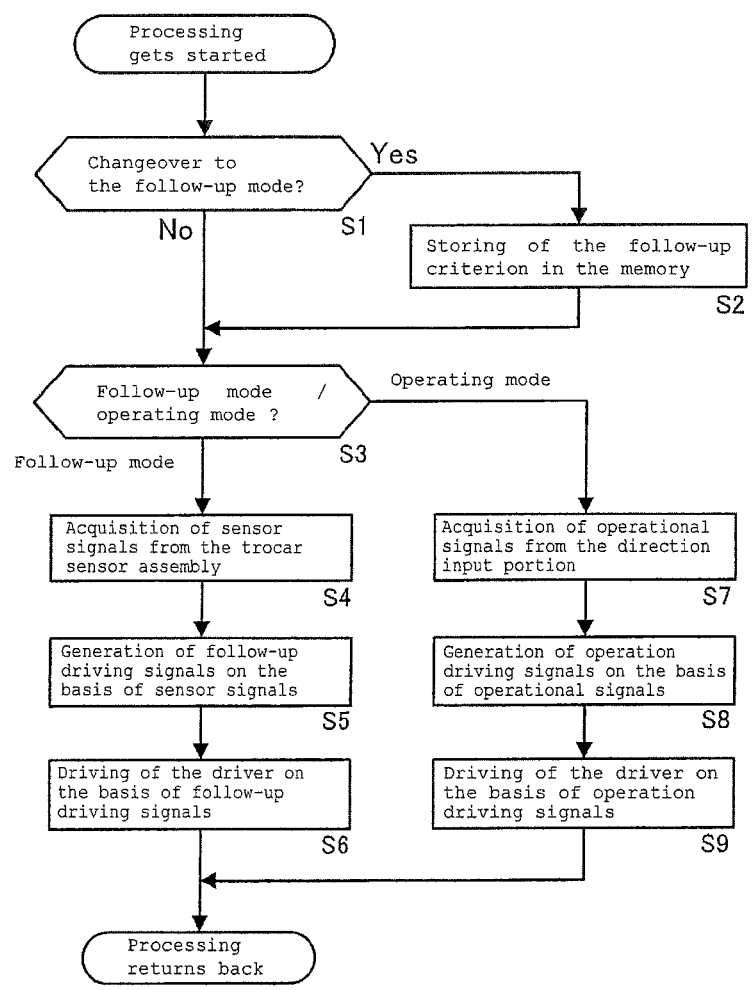
FIG. 8 is a control flowchart for the medical system according to one embodiment of the invention.

FIG. 8 is a control flowchart for the medical system according to the embodiment of the invention described here. In the embodiment described here, the mode input portion 21*b* is operated for a changeover from the operating mode to the follow-up mode (S1: YES), whereupon the follow-up criterion based on the state of the medical instrument 2 is stored in the memory 32 (S2). The state of the medical instrument 2 is detected by the sensors located in the trocar sensor assembly 12 or medical instrument 2 or through the amount-of-rotation information from the moving joint 25 or the like. In the example of FIGS. 7A-7B, the direction in which the distal-end grip 26 points is determined on the basis of a sensor signal from the trocar sensor assembly 12 so that a surface orthogonal to that direction is set as the reference surface St.

With the control processing set in the follow-up mode (S3: Follow-Up Mode), a sensor signal (here a sensor signal produced out of the trocar sensor assembly 12) based on the state of the medical instrument 2 is acquired (S4) to generate a follow-up driving signal that permits the end effector to follow the follow-up criterion stored in the memory on the basis of the sensor signal (S5). As the driver 22 is controlled by this follow-up driving signal (S6), it permits the end effector to maintain a given position relation to the follow-up criterion.

With the control processing set in the operating mode (S3: Operating Mode), on the other hand, the controller 3 receives an operational signal produced out of the direction input portion 21*a* located in the medical instrument 2 (S7) to generate an operation driving signal based on the operational signal (S8). The driver 22 is driven on the basis of the operation driving signal to adjust the angle of the end effector by operation of the direction input portion 21*a*.

Figure 9A:
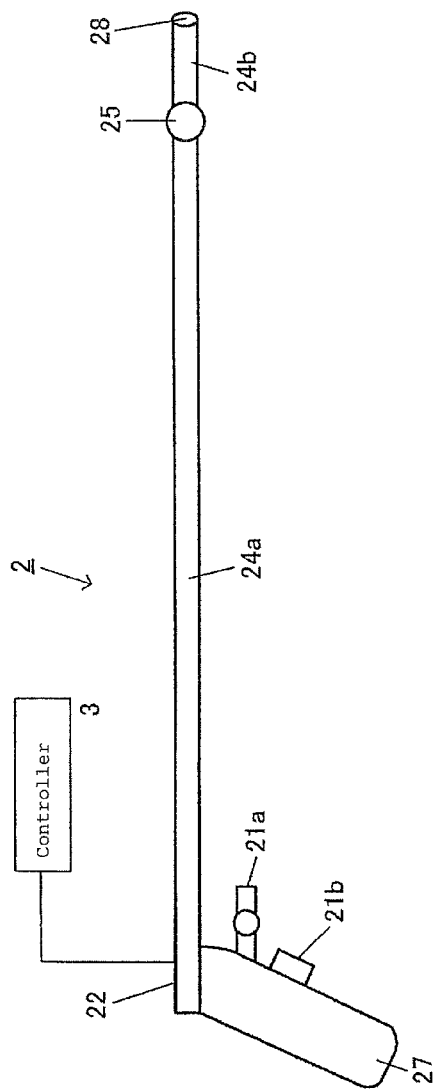
FIGS. 9A and 9B are illustrative of the construction and control mode of the medical system (endoscope) according to one embodiment of the invention.
Figure 9B:
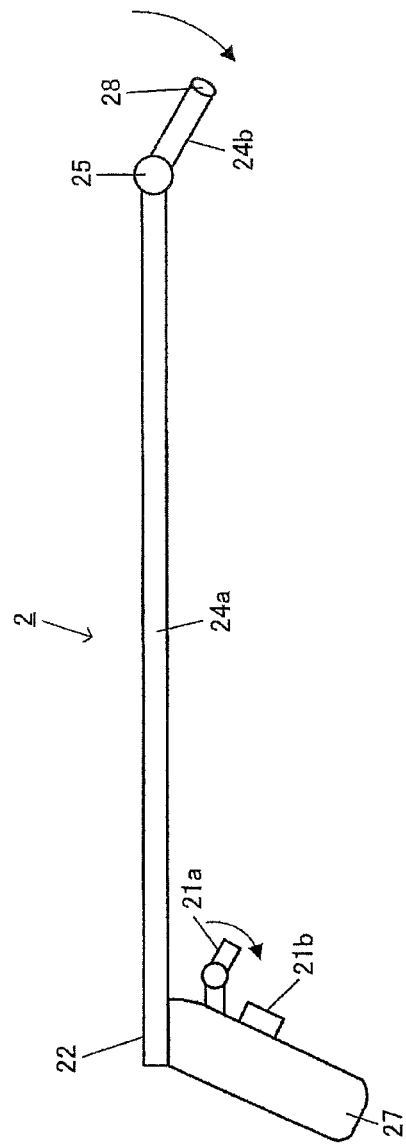

FIGS. 5A-5C show a pair of forceps as one example of the medical instrument 2; however, it is to be noted that in addition to the forceps, there may also be an endoscope used for the purpose of viewing an affected site in the body. FIGS. 9A-9B show the construction and control mode of the medical instrument 2 (endoscope) according to the embodiment described here. FIG. 9A shows connections to the controller 3; so does FIG. 9B although not shown. The endoscope as the medical instrument 2 includes a first shaft 24*a* coupled to a grip member 27, and a second shaft 24*b* rotatably coupled to the first shaft 24*a* via a moving joint 25. The second shaft 24*b* is provided at the distal end with an imager 28 as an end effector. An image signal taken by the imager 28 is sent out to the controller 3 to show the image signal on a monitor or other display, through which the practitioner may view what happens in the body.

As is the case with the forceps, the grip member 27 includes a direction input portion 21*a* and a mode input portion 21*b* so that the practitioner may adjust the direction of the imager 28 and perform mode changeover operation. As shown in FIG. 9B, the moving joint 25 rotates on the basis of operation of the direction input portion 21*a* to adjust the imaging direction of the imager 28. While the moving joint 25 is shown to be capable of two-dimensional motion on the sheet plane, it is to be understood that it may also be capable of three-dimensional motion including a direction orthogonal to the sheet plane.

Figure 10B:
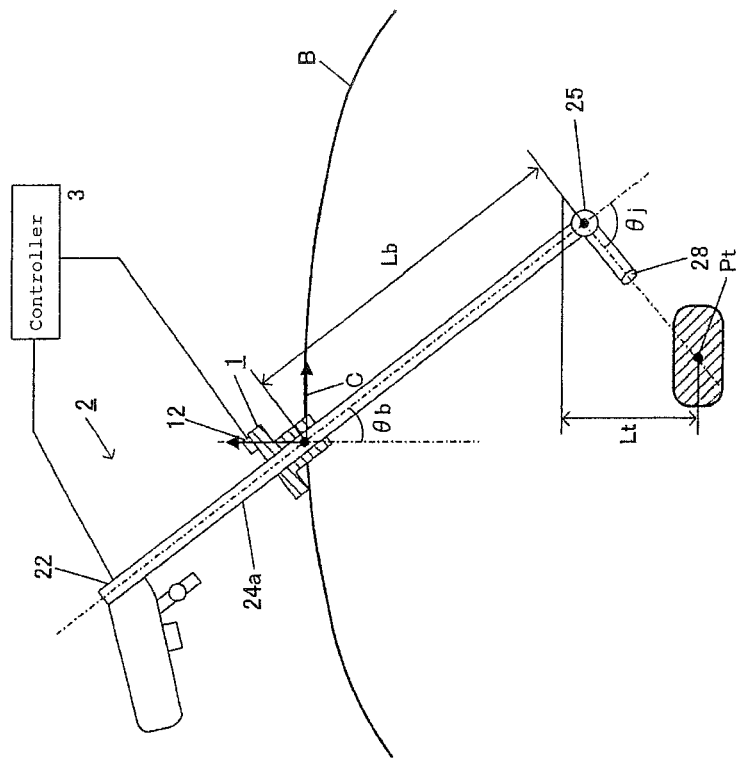
FIGS. 10A and 10B are illustrative of the control mode (Example 2) of the medical instrument according to one embodiment of the invention.
Figure 10A:
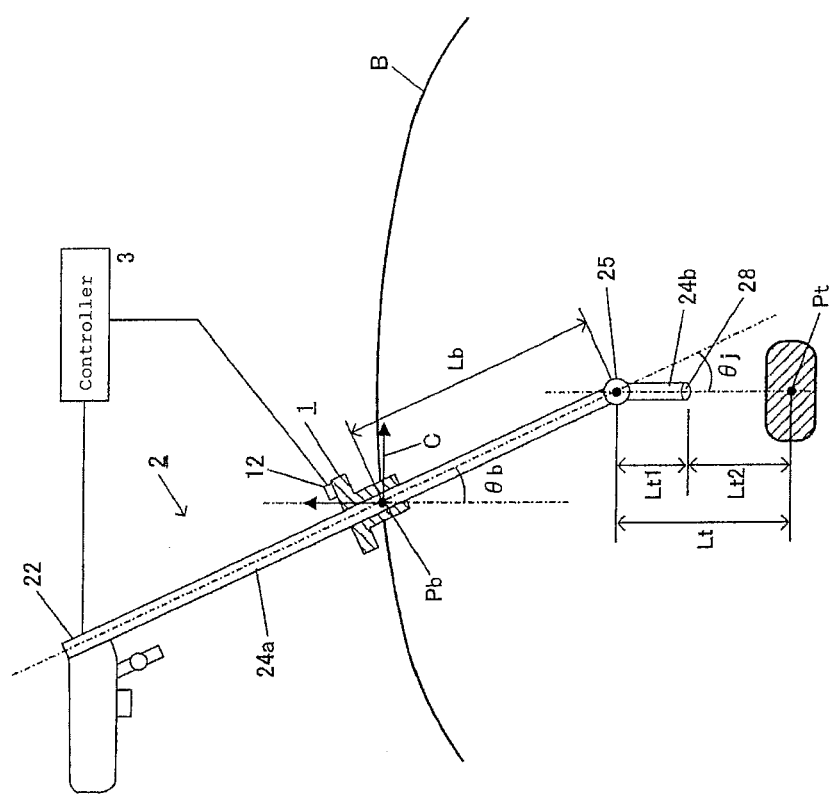

FIGS. 10A-10B show the control mode (Example 2) of the medical instrument according to a specific embodiment of the invention. In this control mode, the endoscope explained with reference to FIGS. 9A-9B is used as the medical instrument 2. The medical instrument 2 and trocar sensor assembly 12 are connected to the controller 3. The controller 3 may detect various states of the medical instrument 2, and drive and control the driver 22 of the medical instrument 2. The control mode of FIGS. 7A-7B is different from this control mode: the reference surface St is set as the follow-up criterion in the former whereas the reference point Pt is set as the follow-up criterion in the latter. When the endoscope is used as the medical instrument 2, the imager 28 as an end effector is controlled in such a way as to point to the set reference point Pt.

Upon movement of the medical instrument 2 from FIG. 10A to FIG. 10B, the angle of the moving joint 25 is driven and adjusted in the follow-up mode such that the imaging direction of the imager 28 points constantly to the reference point Pt. In the mode wherein the reference surface St explained with reference to FIGS. 7A-7B is traced up, the sensor must be used to detect the direction of the first shaft 24*a*, whereas in the mode wherein the reference point Pt is traced up, the position of the end effector must be set on the reference coordinate system.

While FIG. 10A shows that the second shaft 24*b* is orthogonal to the reference point Pt, the reference point Pt of interest to the imager 28 is set in a position spaced away from the imager 28 by a given distance Lt2. This distance Lt2 may be set as a focal position of the imager 28. Alternatively, the practitioner may operate the setting input portion to set the distance Lt2, or a range sensor or image information may be used to measure a distance to the site of interest thereby setting the distance Lt2. Because the length Lt1 of the second shaft 24*b* is a known number, the distance Lt from the reference point Pt to the moving joint 25 may be calculated as the sum of both (Lt1+Lt2). The angle $\theta j$ of the moving joint 25 controlled in the follow-up processing may be figured out using the distance Lt, the amount of movement Lb of the first shaft 24*a*, and the angle $\theta b$ of the first shaft 24a with respect to the reference coordinate system. Note here that while the motion of the moving joint 25 is described in FIGS. 10A-10B as two-dimensional motion on the sheet plane, it is to be noted that in the follow-up mode, the moving joint may also keep up with three-dimensional motion including a direction orthogonal to the sheet plane.

Even when there are changes in the amount of movement Lb of the medical instrument 2 and the angle θb of the first shaft 24 with respect to the reference coordinate system during movement from FIGS. 10A to FIG. 10B, the angle θj of the moving joint 25 may then be driven and controlled such that the imager 28 as the end effector points constantly to the reference point; so the practitioner may view the reference point Pt. In such a control mode, the position of the endoscope may be varied to view the reference point Pt from a variety of angles.

Further in the mode of using the reference point Pt as the follow-up criterion, image-shake resulting from the grip 27 is effectively prevented. In the follow-up processing of the endoscope, the imager 28 follows the reference point Pt even when there is image shake, so that shake of images under observation is prevented, leading to improvements in visibility of the practitioner, etc. Prevention of image shape is effective for not only endoscopes but also for other medical instruments 2 such as a pair of forceps explained with reference to FIGS. 5A-5C.

In the control mode of FIGS. 6 and 8, the mode input portion 21b is operated for a changeover between the operating mode and the follow-up mode. It is here to be noted, however, that the mode changeover may be performed automatically after detection of image shakes resulting from the medical instrument 2. In the embodiment of FIG. 6, whether or not image shakes result from the medical instrument 2 may be detected by processing of a sensor signal from any one of the tilt angle detection sensor 121, amount-of-movement detection sensor 122 and amount-of-rotation detection sensor 123 in the trocar sensor assembly 12 or multi-processing of at least two sensor signals to detect a change in the amount of movement of the medical instrument 2 with time.

In other words, when the change with time in the amount of movement of the medical instrument 2 is within a given frequency, it is determined as the operation of movement by the practitioner for a changeover to the operating mode. When the change with time in the amount of movement of the medical instrument 2 is greater than the given frequency, on the other hand, it is determined as the generation of image shakes for a changeover to the follow-up mode. Such an automatic changeover between the operating mode and the follow-up mode on the basis of the amount of movement of the medical instrument 2 detected by the trocar sensor assembly 12 permits for improved operability of the practitioner. While the trocar sensor assembly 12 is used as the sensor for detection of the amount of movement of the medical instrument 2 for the purpose of detecting image shakes, it is to be noted that other sensor located in the medical instrument 2 may also be used.

While some embodiments according to certain aspects of the invention have been described, it is to be appreciated that the invention is by no means limited to them, and optional combinations of constructions thereof are included in the category of the invention too.

EXPLANATION OF THE REFERENCE NUMERALS

1: Trocar
111: Upper housing
112: Lower housing
113: Tubular member
114: Cable
115: Insertion opening
116: Couplers
12: Trocar sensor assembly
121: Tilt angle detection sensor
122: Amount-of-movement detection sensor
122a: Amount-of-movement detection roller
122b: Photosensor
123: Amount-of-rotation detection sensor
123a: Amount-of-rotation detection roller
123b: Photosensor
13: Communication unit
2: Medical instrument
21: Operation input portion
21a: Direction input portion
21b: Mode input portion
22: Driver
24a: First shaft
24b: Second shaft
25: Moving joint
26: Distal-end grip (end effector)
27, 27a, 27b: Grip members
28: Imager
3: Controller
31: Control unit
32: Memory

What is claimed is:

1. A medical system comprising:
a medical instrument including a shaft coupled to a grip grasped by a user, an end effector located at a distal end of the shaft, a moving joint for adjusting an angle of the end effector relative to the shaft, and a driver for driving the moving joint;
a trocar having an insertion opening through which the medical instrument is inserted;
a sensor assembly for producing a sensor signal including at least an angle of the shaft in a reference coordinate system; and
a controller that enables follow-up processing for driving the driver such that based on the sensor signal produced out of the sensor, the angle of the end effector follows a follow-up criterion in the reference coordinate system.

2. A medical system as recited in claim 1, wherein:
the follow-up criterion is a reference surface set relative to the reference coordinate system; and
the follow-up processing drives the driver such that the end effector has a given configuration relation to the reference surface.

3. A medical system as recited in claim 1, wherein the sensor assembly includes a tilt angle detection sensor located in the trocar or the medical instrument.

4. A medical system as recited in claim 1, wherein:
the sensor assembly produces a sensor signal capable of specifying a position of the end effector in the reference coordinate system;
the follow-up criterion is a reference point set relative to the reference coordinate system; and
the follow-up processing drives the driver such that the end effector has a given configuration relation to the reference point.

5. A medical system as recited in claim 4, wherein the sensor assembly includes an amount-of-movement detection sensor for detecting an amount of rectilinear movement of the medical instrument relative to the trocar.

6. A medical system as recited in claim 4, wherein
the sensor assembly includes an amount-of-rotation detection sensor for detecting an amount of rotation of the medical instrument relative to the trocar.

7. A medical system as recited in claim 1, which comprises a direction input portion of producing an operational signal based on operation, wherein the controller enables operation processing that drives the driver based on an operational signal from the direction input portion to adjust an angle of the end effector.

8. A medical system as recited in claim 7, which comprises a mode input portion of producing an operational signal based on operation, wherein the controller enables changeover processing that implements a changeover between the follow-up processing and the operation processing based on a mode signal from the mode input portion.

9. A medical system as recited in claim 8, wherein the controller enables processing for setting the follow-up criterion upon a changeover from the operation processing to the follow-up processing in the changeover processing.

10. A medical system as recited in claim 7, wherein the controller enables automatic changeover processing for implementing a changeover between the follow-up processing and the operation processing based on a sensor signal produced out of the sensor assembly.

11. A medical system as recited in claim 1, which comprises a setting input portion for producing a setting signal based on operation, wherein:
the controller enables setting processing for setting the follow-up criterion based on a setting signal from the setting input portion.

12. A method of controlling a medical instrument
which includes a shaft coupled to a grip grasped by a user, an end effector located at a distal end of the shaft, a moving joint for adjusting an angle of the end effector relative to the shaft, and a driver for driving the moving joint, comprising:
driving the driver such that the angle of the end effector follows a follow-up criterion in a reference coordinate system based on a sensor signal including at least an angle of the shaft in the reference coordinate system, when the shaft inserted through an insertion opening in a trocar.

* * * * *